United States Patent
Miyakawa et al.

(10) Patent No.: US 9,045,531 B2
(45) Date of Patent: Jun. 2, 2015

(54) HLA-BINDING PEPTIDE, PRECURSOR THEREOF, AND DNA FRAGMENT AND RECOMBINANT VECTOR CODING FOR SAID HLA-BINDING PEPTIDE

(75) Inventors: Tomoya Miyakawa, Tokyo (JP); Keiko Udaka, Kochi (JP)

(73) Assignees: NEC CORPORATION, Tokyo (JP); Kochi University, Tokyo (JP)

( * ) Notice: Subject to any disclaimer, the term of this patent is extended or adjusted under 35 U.S.C. 154(b) by 102 days.

(21) Appl. No.: 12/947,624

(22) Filed: Nov. 16, 2010

(65) Prior Publication Data

US 2011/0087005 A1      Apr. 14, 2011

Related U.S. Application Data

(62) Division of application No. 12/278,348, filed as application No. PCT/JP2007/000058 on Feb. 6, 2007, now abandoned.

(30) Foreign Application Priority Data

Feb. 7, 2006      (JP) ................................. 2006-030227

(51) Int. Cl.
| | | |
|---|---|---|
| *A61K 38/08* | (2006.01) | |
| *C07K 7/06* | (2006.01) | |
| *C07K 14/005* | (2006.01) | |
| *A61K 39/145* | (2006.01) | |
| *A61K 38/00* | (2006.01) | |

(52) U.S. Cl.
CPC ............... *C07K 14/005* (2013.01); *A61K 38/08* (2013.01); *A61K 38/00* (2013.01); *A61K 39/145* (2013.01); *C07K 7/06* (2013.01); *C12N 2760/16022* (2013.01); *C12N 2760/16034* (2013.01)

(58) Field of Classification Search
None
See application file for complete search history.

(56) References Cited

U.S. PATENT DOCUMENTS

| | | | |
|---|---|---|---|
| 6,037,135 A | 3/2000 | Kubo et al. | |
| 6,555,652 B1 | 4/2003 | Itoh et al. | |
| 7,011,833 B1 * | 3/2006 | Sturmhoefel et al. | ..... 424/154.1 |

FOREIGN PATENT DOCUMENTS

| | | | |
|---|---|---|---|
| JP | 05-336960 A | | 12/1993 |
| JP | 8-500106 A | | 1/1996 |
| JP | 8-504168 A | | 5/1996 |
| JP | 8-507080 A | | 7/1996 |
| JP | 8-507525 A | | 8/1996 |
| JP | 10-501791 A | | 2/1998 |
| JP | 10-298198 A | | 11/1998 |
| JP | 11-318455 A | | 11/1999 |
| JP | 2000-116383 A | | 4/2000 |
| JP | 2001-504799 A | | 4/2001 |
| JP | 2004141154 A | * | 5/2004 |
| WO | 94/03205 A1 | | 2/1994 |
| WO | 99/29715 A1 | | 6/1999 |
| WO | WO 01/60849 | * | 8/2001 |

OTHER PUBLICATIONS

Liu et al., Avian Pathology, 2003, 32(5):551-560.*
Japanese Office Action dated Apr. 17, 2012 issued in Japanese Application No. 2007-557758.
Mireille Toebes et al., "Design and use of conditional MHC class I ligands", Nature Medicine, Feb. 5, 2006, vol. 12, No. 2, pp. 246-251.
Office Action dated Feb. 12, 2014, issued by the Japan Patent Office in corresponding Japanese Application No. 2012-135797.

* cited by examiner

*Primary Examiner* — Nicole Kinsey White
(74) *Attorney, Agent, or Firm* — Sughrue Mion, PLLC

(57) ABSTRACT

An HLA-binding peptide binding to an HLA-A type molecule is provided that includes one or more types of amino acid sequence selected from the group consisting of SEQ ID NOS: 1 to 52, and not less than 8 and not more than 11 amino acid residues. All of these amino acid sequences are amino acid sequences predicted to bind to a human HLA-A molecule using a prediction program employing an active learning experiment method shown in FIG. 1.

3 Claims, 1 Drawing Sheet

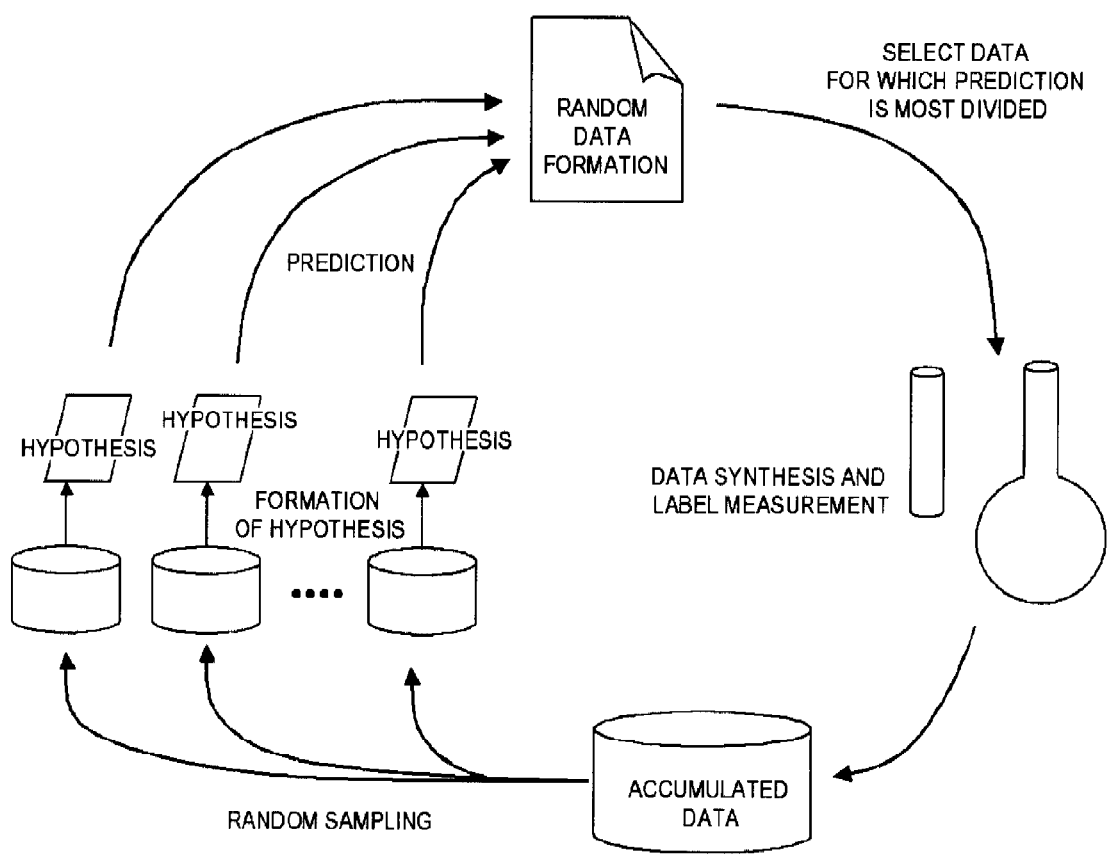

SEQUENCE LISTING

```
<160> NUMBER OF SEQ ID NOS: 55

<210> SEQ ID NO 1
<211> LENGTH: 9
<212> TYPE: PRT
<213> ORGANISM: Influenza A virus

<400> SEQUENCE: 1

Trp Met Ala Cys His Ser Ala Ala Phe
1               5

<210> SEQ ID NO 2
<211> LENGTH: 9
<212> TYPE: PRT
<213> ORGANISM: Influenza A virus

<400> SEQUENCE: 2
```

Arg Leu Leu Gln Asn Ser Gln Val Phe
1               5

<210> SEQ ID NO 3
<211> LENGTH: 9
<212> TYPE: PRT
<213> ORGANISM: Influenza A virus

<400> SEQUENCE: 3

Arg Leu Ile Gln Asn Ser Ile Thr Ile
1               5

<210> SEQ ID NO 4
<211> LENGTH: 9
<212> TYPE: PRT
<213> ORGANISM: Influenza A virus

<400> SEQUENCE: 4

Ile Phe Leu Ala Arg Ser Ala Leu Ile
1               5

<210> SEQ ID NO 5
<211> LENGTH: 9
<212> TYPE: PRT
<213> ORGANISM: Influenza A virus

<400> SEQUENCE: 5

Gly Gln Ile Ser Val Gln Pro Thr Phe
1               5

<210> SEQ ID NO 6
<211> LENGTH: 9
<212> TYPE: PRT
<213> ORGANISM: Influenza A virus

<400> SEQUENCE: 6

Ala Thr Asn Pro Ile Val Pro Ser Phe
1               5

<210> SEQ ID NO 7
<211> LENGTH: 9
<212> TYPE: PRT
<213> ORGANISM: Influenza A virus

<400> SEQUENCE: 7

Ala Thr Asn Pro Val Val Pro Ser Phe
1               5

<210> SEQ ID NO 8
<211> LENGTH: 9
<212> TYPE: PRT
<213> ORGANISM: Influenza A virus

<400> SEQUENCE: 8

Asn Leu Pro Phe Glu Arg Ala Thr Ile
1               5

<210> SEQ ID NO 9
<211> LENGTH: 9
<212> TYPE: PRT
<213> ORGANISM: Influenza A virus

<400> SEQUENCE: 9

Ala Thr Ser Pro Ile Val Pro Ser Phe

<210> SEQ ID NO 10
<211> LENGTH: 9
<212> TYPE: PRT
<213> ORGANISM: Influenza A virus

<400> SEQUENCE: 10

Ile Tyr Arg Arg Arg Asp Gly Lys Trp
1               5

<210> SEQ ID NO 11
<211> LENGTH: 9
<212> TYPE: PRT
<213> ORGANISM: Influenza A virus

<400> SEQUENCE: 11

Ser Leu Pro Phe Glu Arg Ala Thr Ile
1               5

<210> SEQ ID NO 12
<211> LENGTH: 9
<212> TYPE: PRT
<213> ORGANISM: Influenza A virus

<400> SEQUENCE: 12

Val Gly Ile Asp Pro Phe Arg Leu Leu
1               5

<210> SEQ ID NO 13
<211> LENGTH: 9
<212> TYPE: PRT
<213> ORGANISM: Influenza A virus

<400> SEQUENCE: 13

Ile Tyr Lys Arg Arg Glu Gly Lys Trp
1               5

<210> SEQ ID NO 14
<211> LENGTH: 9
<212> TYPE: PRT
<213> ORGANISM: Influenza A virus

<400> SEQUENCE: 14

Arg Met Val Gly Gly Ile Gly Arg Phe
1               5

<210> SEQ ID NO 15
<211> LENGTH: 9
<212> TYPE: PRT
<213> ORGANISM: Influenza A virus

<400> SEQUENCE: 15

Arg Met Val Ser Gly Ile Gly Arg Phe
1               5

<210> SEQ ID NO 16
<211> LENGTH: 9
<212> TYPE: PRT
<213> ORGANISM: Influenza A virus

<400> SEQUENCE: 16

Asp Met Ser Asn Glu Gly Ser Tyr Phe
1               5

```
<210> SEQ ID NO 17
<211> LENGTH: 9
<212> TYPE: PRT
<213> ORGANISM: Influenza A virus

<400> SEQUENCE: 17

Ile Tyr Lys Arg Arg Asp Gly Lys Trp
1               5

<210> SEQ ID NO 18
<211> LENGTH: 9
<212> TYPE: PRT
<213> ORGANISM: Influenza A virus

<400> SEQUENCE: 18

Asp Met Asn Asn Glu Gly Ser Tyr Phe
1               5

<210> SEQ ID NO 19
<211> LENGTH: 9
<212> TYPE: PRT
<213> ORGANISM: Influenza A virus

<400> SEQUENCE: 19

Ala Glu Ile Glu Asp Leu Ile Phe Leu
1               5

<210> SEQ ID NO 20
<211> LENGTH: 9
<212> TYPE: PRT
<213> ORGANISM: Influenza A virus

<400> SEQUENCE: 20

Ile Glu Arg Met Val Leu Ser Ala Phe
1               5

<210> SEQ ID NO 21
<211> LENGTH: 9
<212> TYPE: PRT
<213> ORGANISM: Influenza A virus

<400> SEQUENCE: 21

Tyr Leu Glu Glu His Pro Ser Ala Gly
1               5

<210> SEQ ID NO 22
<211> LENGTH: 9
<212> TYPE: PRT
<213> ORGANISM: Influenza A virus

<400> SEQUENCE: 22

Ser Leu Pro Phe Glu Arg Ala Thr Ile
1               5

<210> SEQ ID NO 23
<211> LENGTH: 9
<212> TYPE: PRT
<213> ORGANISM: Influenza A virus

<400> SEQUENCE: 23

Ala Val Lys Gly Val Gly Thr Met Val
1               5

<210> SEQ ID NO 24
```

```
<211> LENGTH: 9
<212> TYPE: PRT
<213> ORGANISM: Influenza A virus

<400> SEQUENCE: 24

Phe Arg Leu Leu Gln Asn Ser Gln Val
1               5

<210> SEQ ID NO 25
<211> LENGTH: 9
<212> TYPE: PRT
<213> ORGANISM: Influenza A virus

<400> SEQUENCE: 25

Asn Leu Pro Phe Glu Arg Ala Thr Ile
1               5

<210> SEQ ID NO 26
<211> LENGTH: 9
<212> TYPE: PRT
<213> ORGANISM: Influenza A virus

<400> SEQUENCE: 26

Tyr Leu Glu Glu Asn Pro Ser Ala Gly
1               5

<210> SEQ ID NO 27
<211> LENGTH: 9
<212> TYPE: PRT
<213> ORGANISM: Influenza A virus

<400> SEQUENCE: 27

Ala Val Lys Gly Ile Gly Thr Met Val
1               5

<210> SEQ ID NO 28
<211> LENGTH: 9
<212> TYPE: PRT
<213> ORGANISM: Influenza A virus

<400> SEQUENCE: 28

Arg Leu Ile Gln Asn Ser Ile Thr Ile
1               5

<210> SEQ ID NO 29
<211> LENGTH: 9
<212> TYPE: PRT
<213> ORGANISM: Influenza A virus

<400> SEQUENCE: 29

Ser Ser Phe Ile Arg Gly Thr Arg Val
1               5

<210> SEQ ID NO 30
<211> LENGTH: 9
<212> TYPE: PRT
<213> ORGANISM: Influenza A virus

<400> SEQUENCE: 30

Trp Met Ala Cys His Ser Ala Ala Phe
1               5

<210> SEQ ID NO 31
<211> LENGTH: 9
<212> TYPE: PRT
```

```
<213> ORGANISM: Influenza A virus

<400> SEQUENCE: 31

Phe Leu Ala Arg Ser Ala Leu Ile Leu
1               5

<210> SEQ ID NO 32
<211> LENGTH: 9
<212> TYPE: PRT
<213> ORGANISM: Influenza A virus

<400> SEQUENCE: 32

Cys Leu Pro Ala Cys Val Tyr Gly Leu
1               5

<210> SEQ ID NO 33
<211> LENGTH: 9
<212> TYPE: PRT
<213> ORGANISM: Influenza A virus

<400> SEQUENCE: 33

Ser Ala Leu Ile Leu Arg Gly Ser Val
1               5

<210> SEQ ID NO 34
<211> LENGTH: 9
<212> TYPE: PRT
<213> ORGANISM: Influenza A virus

<400> SEQUENCE: 34

Ala Gln Arg Ala Met Met Asp Gln Val
1               5

<210> SEQ ID NO 35
<211> LENGTH: 9
<212> TYPE: PRT
<213> ORGANISM: Influenza A virus

<400> SEQUENCE: 35

Ile Phe Leu Ala Arg Ser Ala Leu Ile
1               5

<210> SEQ ID NO 36
<211> LENGTH: 9
<212> TYPE: PRT
<213> ORGANISM: Influenza A virus

<400> SEQUENCE: 36

Asn Ala Thr Glu Ile Arg Ala Ser Val
1               5

<210> SEQ ID NO 37
<211> LENGTH: 9
<212> TYPE: PRT
<213> ORGANISM: Influenza A virus

<400> SEQUENCE: 37

Ser Ala Leu Ile Leu Arg Gly Ser Val
1               5

<210> SEQ ID NO 38
<211> LENGTH: 9
<212> TYPE: PRT
<213> ORGANISM: Influenza A virus
```

```
<400> SEQUENCE: 38

Ala Val Lys Gly Val Gly Thr Met Val
1               5

<210> SEQ ID NO 39
<211> LENGTH: 9
<212> TYPE: PRT
<213> ORGANISM: Influenza A virus

<400> SEQUENCE: 39

Met Val Leu Ser Ala Phe Asp Glu Arg
1               5

<210> SEQ ID NO 40
<211> LENGTH: 9
<212> TYPE: PRT
<213> ORGANISM: Influenza A virus

<400> SEQUENCE: 40

Ala Gln Arg Ala Met Met Asp Gln Val
1               5

<210> SEQ ID NO 41
<211> LENGTH: 9
<212> TYPE: PRT
<213> ORGANISM: Influenza A virus

<400> SEQUENCE: 41

Ala Val Lys Gly Ile Gly Thr Met Val
1               5

<210> SEQ ID NO 42
<211> LENGTH: 9
<212> TYPE: PRT
<213> ORGANISM: Influenza A virus

<400> SEQUENCE: 42

Ala Thr Ile Met Ala Ala Phe Thr Gly
1               5

<210> SEQ ID NO 43
<211> LENGTH: 9
<212> TYPE: PRT
<213> ORGANISM: Influenza A virus

<400> SEQUENCE: 43

Asn Ala Thr Glu Ile Arg Ala Ser Val
1               5

<210> SEQ ID NO 44
<211> LENGTH: 9
<212> TYPE: PRT
<213> ORGANISM: Influenza A virus

<400> SEQUENCE: 44

Arg Thr Ser Asp Met Arg Thr Glu Ile
1               5

<210> SEQ ID NO 45
<211> LENGTH: 9
<212> TYPE: PRT
<213> ORGANISM: Influenza A virus

<400> SEQUENCE: 45
```

Arg Leu Ile Gln Asn Ser Ile Thr Ile
1               5

<210> SEQ ID NO 46
<211> LENGTH: 9
<212> TYPE: PRT
<213> ORGANISM: Influenza A virus

<400> SEQUENCE: 46

Ala Ala Gly Ala Ala Val Lys Gly Val
1               5

<210> SEQ ID NO 47
<211> LENGTH: 9
<212> TYPE: PRT
<213> ORGANISM: Influenza A virus

<400> SEQUENCE: 47

Phe Arg Leu Leu Gln Asn Ser Gln Val
1               5

<210> SEQ ID NO 48
<211> LENGTH: 9
<212> TYPE: PRT
<213> ORGANISM: Influenza A virus

<400> SEQUENCE: 48

Phe Gln Gly Arg Gly Val Phe Glu Leu
1               5

<210> SEQ ID NO 49
<211> LENGTH: 9
<212> TYPE: PRT
<213> ORGANISM: Influenza A virus

<400> SEQUENCE: 49

Leu Gln Asn Ser Gln Val Phe Ser Leu
1               5

<210> SEQ ID NO 50
<211> LENGTH: 9
<212> TYPE: PRT
<213> ORGANISM: Influenza A virus

<400> SEQUENCE: 50

Phe Leu Ala Arg Ser Ala Leu Ile Leu
1               5

<210> SEQ ID NO 51
<211> LENGTH: 9
<212> TYPE: PRT
<213> ORGANISM: Influenza A virus

<400> SEQUENCE: 51

Leu Ile Leu Tyr Asp Lys Glu Glu Ile
1               5

<210> SEQ ID NO 52
<211> LENGTH: 9
<212> TYPE: PRT
<213> ORGANISM: Influenza A virus

<400> SEQUENCE: 52

Leu Ile Phe Leu Ala Arg Ser Ala Leu
1               5

<210> SEQ ID NO 53
<211> LENGTH: 498
<212> TYPE: PRT
<213> ORGANISM: Influenza A virus

<400> SEQUENCE: 53

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Arg Asp Gly Lys Trp Met Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

```
Glu Asn Met Glu Thr Met Asp Ser Ser Thr Leu Glu Leu Arg Ser Arg
        370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Asn Pro Val Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 54
<211> LENGTH: 497
<212> TYPE: PRT
<213> ORGANISM: Influenza A virus

<400> SEQUENCE: 54

Met Ala Leu Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
                20                  25                  30

Val Gly Gly Ile Gly Arg Phe Tyr Ile Gln Met Cys Thr Glu Leu Lys
            35                  40                  45

Leu Ser Asp His Glu Gly Arg Leu Ile Gln Asn Ser Ile Thr Ile Glu
        50                  55                  60

Arg Met Val Leu Ser Ala Phe Asp Glu Arg Arg Asn Arg Tyr Leu Glu
65                  70                  75                  80

Glu Asn Pro Ser Ala Gly Lys Asp Pro Lys Lys Thr Gly Gly Pro Ile
                85                  90                  95

Tyr Lys Arg Arg Glu Gly Lys Trp Val Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Ile Lys Arg Gly Ile Asn Asp Arg Asn Phe Trp Arg
        195                 200                 205

Gly Asp Asn Gly Arg Arg Thr Arg Ile Ala Tyr Glu Arg Met Cys Asn
    210                 215                 220

Ile Leu Lys Gly Lys Phe Gln Thr Glu Ala Gln Arg Ala Met Met Asp
225                 230                 235                 240
```

-continued

Gln Val Arg Glu Ser Arg Asn Pro Gly Asn Ala Glu Ile Glu Asp Leu
            245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
            275                 280                 285

Tyr Asp Phe Glu Arg Glu Gly Tyr Ser Leu Val Gly Ile Asp Pro Phe
            290                 295                 300

Arg Leu Leu Gln Asn Ser Gln Val Phe Ser Leu Ile Arg Ser Asn Glu
305                 310                 315                 320

Asn Pro Ala His Lys Ser Gln Leu Val Trp Met Ala Cys His Ser Ala
            325                 330                 335

Ala Phe Glu Asp Leu Arg Val Ser Ser Phe Ile Arg Gly Thr Arg Val
            340                 345                 350

Ile Pro Arg Gly Gln Leu Ser Thr Arg Gly Val Gln Ile Ala Ser Asn
            355                 360                 365

Glu Asn Met Glu Thr Ile Asp Ser Ser Thr Leu Glu Leu Arg Ser Arg
            370                 375                 380

Tyr Trp Ala Ile Arg Thr Arg Ser Gly Gly Asn Thr Asn Gln His Arg
385                 390                 395                 400

Ala Ser Ala Gly Gln Ile Ser Val Gln Pro Thr Phe Ser Val Gln Arg
            405                 410                 415

Ser Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
            435                 440                 445

Glu Asn Ala Lys Pro Glu Asp Val Ser Phe Gln Gly Arg Gly Val Phe
            450                 455                 460

Glu Leu Ser Asp Glu Lys Ala Thr Ser Pro Ile Val Pro Ser Phe Asp
465                 470                 475                 480

Met Ser Asn Glu Gly Ser Tyr Phe Phe Gly Asp Asn Ala Glu Glu Tyr
            485                 490                 495

Asp

<210> SEQ ID NO 55
<211> LENGTH: 498
<212> TYPE: PRT
<213> ORGANISM: Influenza A virus

<400> SEQUENCE: 55

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Ser Gly Ile Gly Arg Phe Tyr Ile Gln Met Cys Thr Glu Leu Lys
            35                  40                  45

Leu Ser Asp Tyr Glu Gly Arg Leu Ile Gln Asn Ser Ile Thr Ile Glu
            50                  55                  60

Arg Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
            85                  90                  95

```
Tyr Arg Arg Arg Asp Gly Lys Trp Val Arg Glu Leu Ile Leu Tyr Asp
                100                 105                 110

Lys Glu Glu Ile Arg Arg Ile Trp Arg Gln Ala Asn Gly Glu Asp
            115                 120                 125

Ala Thr Ala Gly Leu Thr His Leu Met Ile Trp His Ser Asn Leu Asn
130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
            195                 200                 205

Gly Glu Asn Gly Arg Arg Thr Arg Ile Ala Tyr Glu Arg Met Cys Asn
            210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
                260                 265                 270

Lys Ser Cys Leu Pro Ala Cys Val Tyr Gly Leu Ala Val Ala Ser Gly
            275                 280                 285

Tyr Asp Phe Glu Arg Glu Gly Tyr Ser Leu Val Gly Ile Asp Pro Phe
            290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
            355                 360                 365

Glu Asn Met Glu Ala Met Asp Ser Asn Thr Leu Glu Leu Arg Ser Arg
370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
                420                 425                 430

Thr Glu Gly Arg Thr Ser Asp Met Arg Thr Glu Ile Ile Arg Met Met
            435                 440                 445

Glu Ser Ala Arg Pro Glu Asp Val Ser Phe Gln Gly Arg Gly Val Phe
            450                 455                 460

Glu Leu Ser Asp Glu Lys Ala Thr Asn Pro Ile Val Pro Ser Phe Asp
465                 470                 475                 480

Met Asn Asn Glu Gly Ser Tyr Phe Phe Gly Asp Asn Ala Glu Glu Tyr
                485                 490                 495

Asp Asn
```

HLA-BINDING PEPTIDE, PRECURSOR THEREOF, AND DNA FRAGMENT AND RECOMBINANT VECTOR CODING FOR SAID HLA-BINDING PEPTIDE

CROSS REFERENCE TO RELATED APPLICATIONS

This application is a divisional of U.S. Patent Application No. 12/278,348 filed Aug. 5, 2008 (abandoned), which is a national stage of International Application No. PCT/JP2007/000058 filed Feb. 6, 2007, which claims priority from Japanese Patent Application No. 2006-030227 filed Feb. 7, 2006, the contents of all of which are incorporated herein by reference in their entirety.

TECHNICAL FIELD

The present invention relates to HLA-binding peptides, precursors thereof, and DNA fragments and recombinant vectors coding for the HLA-binding peptides.

BACKGROUND ART

When infection with a virus such as an influenza virus occurs, a virus elimination reaction due to natural immunity proceeds, a specific immune response is subsequently induced, and a virus elimination reaction proceeds.

In the specific immune response, virus in a body fluid is eliminated by a neutralizing antibody, and virus within a cell is eliminated by a cytotoxic T lymphocyte (CTL). That is, the CTL specifically recognizes a virus antigen (CTL epitope) consisting of 8 to 11 amino acids presented in an HLA class I molecule on the surface of an infected cell, and eliminates the virus by damaging the infected cell. Identifying such a virus-specific CTL epitope is therefore important for preparing preventive and therapeutic vaccines for the virus.

A technique of this kind is known from Patent Publication 1. Patent Publication 1 states that an oligopeptide formed from a specific amino acid sequence has the property of binding to an HLA.

[Patent Publication 1] Japanese Patent Application Laid-open No. H8-151396 (1996)

DISCLOSURE OF THE INVENTION

However, the conventional technique described in the above-mentioned publication has room for improvement with regard to the following points.

Firstly, it is unclear whether or not the HLA-binding peptide of the above-mentioned publication binds to an HLA molecule effectively, and there is still room for improvement in terms of the HLA-binding properties.

Secondly, it is stated that the HLA-binding peptide of the above-mentioned publication has the property of binding to HLA-DQ4. However, it is unclear whether or not it binds to an HLA-A2 molecule (product of the HLA-A*0201 gene, HLA-A*0206 gene and the like), which is often seen in European and American people, and an HLA-A24 molecule (product of the HLA-A*2402 gene and the like), which is often seen in Japanese people.

The present invention has been accomplished under the above-mentioned circumstances, and provides an HLA-binding peptide that has excellent properties in binding to a specific type of HLA molecule.

According to the present invention, there is provided an HLA-binding peptide binding to an HLA-A type molecule, the HLA-binding peptide containing one or more types of amino acid sequence selected from the group consisting of SEQ ID NOS: 1 to 52, and consisting of not less than 8 and not more than 11 amino acid residues.

Furthermore, according to the present invention, there is provided the HLA-binding peptide, wherein it contains one or more types of amino acid sequence selected from the group consisting of SEQ ID NOS: 1, 2, 3, 4, 5, 6, 7, 8, 9, 10, 11, 12, 13, 14, 15, 16, 17, 18, 21, 22, 23, 24, 25, 26, 27, 28, 30, 31, 34, 35, 36, 37, 38, 40, 41, 43, 45, 47, 48, 49, 50, 51, and 52.

Moreover, according to the present invention, there is provided an HLA-binding peptide binding to an HLA-A type molecule, the HLA-binding peptide containing an amino acid sequence formed by deletion, substitution, or addition of one or two amino acid residues of the amino acid sequence contained in the above-mentioned HLA-binding peptide, and consisting of not less than 8 and not more than 11 amino acid residues.

In this way, the construct containing an amino acid sequence formed by deletion, substitution, or addition of one or a few amino acid residues of a specific amino acid sequence that has the property of binding to an HLA-A type molecule can also exhibit a similar effect to that of the above-mentioned HLA-binding peptide.

Furthermore, according to the present invention, there is provided a DNA fragment containing a DNA sequence coding for the above-mentioned HLA-binding peptide.

Moreover, according to the present invention, there is provided a recombinant vector containing a DNA sequence coding for the above-mentioned HLA-binding peptide.

Furthermore, according to the present invention, there is provided an HLA-binding peptide precursor changing within a mammalian body into the above-mentioned HLA-binding peptide.

In accordance with the present invention, since it contains a specific amino acid sequence, an HLA-binding peptide that has excellent properties in binding to an HLA-A type molecule can be obtained.

BRIEF DESCRIPTION OF THE DRAWINGS

The above-mentioned object, other objects, features, and advantages will become more apparent from preferred embodiments explained below by reference to the attached drawing.

FIG. 1 A schematic drawing for explaining an active learning experiment design used in an embodiment.

BEST MODE FOR CARRYING OUT THE INVENTION

Modes for carrying out the present invention are explained below by reference to a drawing. In the drawing, similar components are denoted by similar reference numerals and symbols, and duplication of explanation is avoided as appropriate.

<Embodiment 1>

In this embodiment a peptide that contains an amino acid sequence for which the binding to an HLA molecule, predicted by a hypothesis obtained using an active learning experiment method (Japanese Patent Application Laid-open No. H11-316754 (1999)), is 3 or greater in terms of a –log Kd value, and consists of not less than 8 and not more than 11 amino acid residues is used as a candidate for an HLA-binding peptide. From the results of carrying out a binding experiment, it has been confirmed that these peptides are actually HLA-binding peptides.

As a result, a large number of HLA-binding peptides that have excellent properties in binding to an HLA-A type molecule because they contain amino acid sequence for which the binding to the HLA molecule in terms of a −log Kd value is 3 or greater could be obtained efficiently.

Specifically, the HLA-binding peptide related to this embodiment is an HLA-binding peptide that binds to an HLA-A type molecule, contains one or more types of amino acid sequence selected from the group consisting of SEQ ID NOS: 1 to 52, which will be described later, and consists of not less than 8 and not more than 11 amino acid residues.

Among human HLA-A types, about 50% of Japanese people have the HLA-A24 type. Many European and American people, such as German people, have the HLA-A2 type.

All of these sequences are sequences consisting of 9 amino acid residues contained in a certain genome protein of an avian influenza virus.

The sequences of SEQ ID NOS: 1 to 20 are given in Table 1 below.

TABLE 1

HLA-A24-binding peptides

| SEQ ID No | SEQ | Predicted Score | SEQ Name | Binding Experiment Data |
|---|---|---|---|---|
| 1 | WMACHSAAF | 6.1873 | 330 | 7.27004 |
| 2 | RLLQNSQVF | 6.0988 | 305 | 6.91461 |
| 3 | RLIQNSITI | 5.9077 | 55 | 7.0483 |
| 4 | IFLARSALI | 5.8166 | 257 | 8.01161 |
| 5 | GQISVQPTF | 5.7493 | 404 | 7.19131 |
| 6 | ATNPIVPSF | 5.6519 | 5-471 | 7.56449 |
| 7 | ATNPVVPSF | 5.6282 | 471 | 7.80781 |
| 8 | NLPFERATI | 5.5547 | 417 | 7.76375 |
| 9 | ATSPIVPSF | 5.5244 | 9-471 | 7.80229 |
| 10 | IYRRRDGKW | 5.514 | 5-96 | 7.49653 |
| 11 | SLPFERATI | 5.4943 | 9-417 | 7.71879 |
| 12 | VGIDPFRLL | 5.3829 | 299 | 5.12018 |
| 13 | IYKRREGKW | 5.3618 | 9-96 | 7.25015 |
| 14 | RMVGGIGRF | 5.3166 | 31 | 7.54336 |
| 15 | RMVSGIGRF | 5.2164 | 5-31 | 7.43594 |
| 16 | DMSNEGSYF | 5.1901 | 480 | 5.74415 |
| 17 | IYKRRDGKW | 5.1812 | 96 | 7.32598 |
| 18 | DMNNEGSYF | 5.169 | 5-480 | 5.37438 |
| 19 | AEIEDLIFL | 5.1369 | 251 | |
| 20 | IERMVLSAF | 5.0612 | 63 | |

The sequences of SEQ ID NOS: 1 to 20 are sequences consisting of 9 amino acid residues contained in a nucleoprotein of M22344 (H7) strain, AF508607 (H9) strain, or AY676037 (H5) strain, which are 3 representative serotypes (H7, H9, H5) of an avian influenza virus, which is described later. The sequences of SEQ ID NOS: 1 to 20 are sequences predicted by the above-mentioned method to be the highest in terms of binding to an HLA-A24 molecule (a product of the HLA-A*2402 gene). SEQ ID NOS: 1 to 20 are arranged in decreasing binding order. That is, SEQ ID NO: 1 is the sequence that is predicted to have the best binding. A predicted score for binding to the HLA-A24 molecule and binding experiment data for each sequence are expressed in the form of −log Kd values.

The sequences of SEQ ID NOS: 21 to 36 are given in Table 2 below.

TABLE 2

HLA-A2-binding peptides

| SEQ ID No | SEQ | Predicted Score | SEQ Name | Binding Experiment Data |
|---|---|---|---|---|
| 21 | YLEEHPSAG | 5.3104 | 78 | 5.08483 |
| 22 | SLPFERATI | 5.3061 | 9-417 | 5.24328 |
| 23 | AVKGVGTMV | 5.083 | 182 | 5.57857 |
| 24 | FRLLQNSQV | 5.0517 | 304 | 4.45468 |
| 25 | NLPFERATI | 5.0017 | 417 | |
| 26 | YLEENPSAG | 4.9503 | 9-78 | 4.90353 |
| 27 | AVKGIGTMV | 4.9476 | 9-182 | 4.8085 |
| 28 | RLIQNSITI | 4.9311 | 55 | 5.0127 |
| 29 | SSFIRGTRV | 4.9002 | 344 | |
| 30 | WMACHSAAF | 4.8588 | 330 | 5.7894 |
| 31 | FLARSALIL | 4.8472 | 258 | 5.4765 |
| 32 | CLPACVYGL | 4.8118 | 275 | |
| 33 | SALILRGSV | 4.7469 | 262 | |
| 34 | AQRAMMDQV | 4.5751 | 234 | 5.33481 |
| 35 | IFLARSALI | 4.5056 | 257 | 5.93818 |
| 36 | NATEIRASV | 4.4764 | 21 | 4.74314 |

The sequences of SEQ ID NOS: 21 to 36 are sequences consisting of 9 amino acid residues contained in a nucleoprotein of M22344 (H7) strain, AF508607 (H9) strain, or AY676037 (H5) strain, which are 3 representative serum types (H7, H9, H5) of an avian influenza virus, which is described later. The sequences of SEQ ID NOS: 21 to 36 are sequences predicted by the above-mentioned method to be the highest in terms of binding to an HLA-A2 molecule (a product of the HLA-A*0201 gene). SEQ ID NOS: 21 to 36 are arranged in decreasing binding order. That is, SEQ ID NO: 21 is the sequence that is predicted to have the best binding. A predicted score for binding to the HLA-A2 molecule and binding experiment data for each sequence are expressed in the form of −log Kd values.

The sequences of SEQ ID NOS: 37 to 52 are given in Table 3 below.

TABLE 3

HLA-A2-binding peptides

| SEQ ID No | SEQ | Predicted Score | SEQ Name | Binding Experiment Data |
|---|---|---|---|---|
| 37 | SALILRGSV | 5.4597 | 262 | 3.83934 |
| 38 | AVKGVGTMV | 5.3312 | 182 | 3.65413 |
| 39 | MVLSAFDER | 5.0975 | 66 | |
| 40 | AQRAMMDQV | 5.0607 | 234 | 5.64316 |
| 41 | AVKGIGTMV | 5.0277 | 9-182 | 3.51984 |
| 42 | ATIMAAFTG | 4.9325 | 423 | |
| 43 | NATEIRASV | 4.9117 | 21 | 5.70368 |
| 44 | RTSDMRTEI | 4.8958 | 436 | |
| 45 | RLIQNSITI | 4.8951 | 55 | 4.42539 |
| 46 | AAGAAVKGV | 4.8858 | 178 | |
| 47 | FRLLQNSQV | 4.7792 | 304 | 4.21314 |
| 48 | FQGRGVFEL | 4.6325 | 458 | 6.77438 |
| 49 | LQNSQVFSL | 4.5655 | 307 | 5.78131 |
| 50 | FLARSALIL | 4.4298 | 258 | 4.34141 |
| 51 | LILYDKEEI | 4.3648 | 108 | 5.38215 |
| 52 | LIFLARSAL | 4.3468 | 256 | 3.73085 |

The sequences of SEQ ID NOS: 37 to 52 are sequences consisting of 9 amino acid residues contained in a nucleoprotein of M22344 (H7) strain, AF508607 (H9) strain, or AY676037 (H5) strain, which are 3 representative serum types (H7, H9, H5) of an avian influenza virus, which is described later. The sequences of SEQ ID NOS: 37 to 52 are sequences predicted by the above-mentioned method to be the highest in terms of binding to an HLA-A2 molecule (a product of the HLA-A*0206 gene). SEQ ID NOS: 37 to 52 are arranged in decreasing binding order. That is, SEQ ID NO: 37 is the sequence that is predicted to have the best binding. A predicted score for binding to the HLA-A2 molecule and binding experiment data for each sequence are expressed in the form of −log Kd values.

Although details are described later, it is clear that in all of Tables 1 to 3 there is a correlation between the predicted score and the binding experiment data. That is, although there are slight errors, it can be said that a peptide that is predicted by the above-mentioned method to have high binding to the HLA-A molecule is found experimentally to have high binding to the HLA-A molecule.

Since there is no conventional technique for discovering an HLA-binding peptide by utilizing such an experimental design method, there are only a very small number of HLA-binding peptides that have been experimentally confirmed to have HLA-binding properties. Because of this, even when a peptide consisting of 9 amino acid residues is randomly synthesized by a conventional method and subjected to an experiment to find out if it binds to an HLA molecule, there is a probability of only about 1 in 100 of finding one that has a binding, in terms of a −log Kd value, exceeding 6.

In accordance with this embodiment, since the technique of finding an HLA-binding peptide by utilizing the experimental design method is used, as described above, as many as 52 sequences of HLA-binding peptides can be found. Furthermore, when the binding of some of the HLA-binding peptides obtained is experimentally examined, it is confirmed that all of the sequences that have been subjected to the experiment exhibit an excellent binding to HLA that is equal to or higher than that predicted.

Among these sequences, an HLA-binding peptide containing one or more types of amino acid sequence selected from the group consisting of SEQ ID NOS: 1, 2, 3, 4, 5, 6, 7, 8, 9, 10, 11, 12, 13, 14, 15, 16, 17, 18, 21, 22, 23, 24, 25, 26, 27, 28, 30, 31, 34, 35, 36, 37, 38, 40, 41, 43, 45, 47, 48, 49, 50, 51, and 52 is experimentally confirmed to bind to a human HLA-A type molecule. It can therefore be said with certainty that it is an HLA-binding peptide that has excellent properties in binding to a human HLA-A type molecule.

The binding to an HLA molecule of the HLA-binding peptide related to the present embodiment is 3 or greater in terms of a −log Kd value, particularly preferably 5 or greater, and more preferably 5.4 or greater.

In the field of biochemistry, it is known that a binding ability, in terms of a −log Kd value, of about 3 is the threshold level for whether or not a peptide actually binds to an MHC, which includes an HLA. Therefore, if the binding to an HLA molecule, in terms of a −log Kd value, is 3 or greater, it can be said that it is an HLA-binding peptide.

Furthermore, in the case of an HLA-A24 molecule, if the binding to the HLA-A24 molecule, in terms of a −log Kd value, is 5 or greater, since the peptide obtained has excellent properties in binding to the HLA molecule, it can suitably be used for the development of an effective therapeutic drug, prophylactic drug, and the like for an immune disease and the like.

Moreover, if the binding to an HLA-A24 molecule, in terms of a −log Kd value, is 5.4 or greater, the peptide obtained has particularly good properties in binding to the HLA molecule, and it can suitably be used for the development of an even more effective therapeutic drug, prophylactic drug, and the like for an immune disease and the like.

Furthermore, it may be arranged that the HLA-binding peptide related to the present embodiment consists of not less than 8 and not more than 11 amino acid residues.

In this way, if the peptide consists of not less than 8 and not more than 11 amino acid residues, it has excellent properties in binding to an HLA molecule. Furthermore, the cytotoxic T lymphocyte (CTL) specifically recognizes a virus antigen (CTL epitope) consisting of 8 to 11 amino acids presented in an HLA class I molecule on the surface of a cell infected with a virus and the like, and eliminates the virus by damaging the infected cell. It is important to prepare such a CTL epitope consisting of 8 to 11 amino acids that is specific to a virus and the like in order to prepare a vaccine for therapy or prevention against the virus and the like.

For example, the above-mentioned HLA-binding peptide may be a peptide consisting of amino acid residues alone, but it is not particularly limited thereto. For example, it may be an HLA-binding peptide precursor that is optionally modified with a sugar chain or a fatty acid group and the like as long as the effects of the present invention are not impaired. Such a precursor is subjected to a change involving digestion by a proteolytic enzyme and the like in a living mammalian body such as in a human digestive organ to become an HLA-binding peptide, thus exhibiting similar effects to those shown by the above-mentioned HLA-binding peptide.

Furthermore, the above-mentioned HLA-binding peptide may be a peptide that binds to a human HLA-A24 molecule.

Moreover, the above-mentioned HLA-binding peptide may also be a peptide that binds to a human HLA-A2 molecule.

In accordance with this constitution, since a peptide is obtained that binds to an HLA-A24 molecule, which is often seen in Asian people, such as Japanese people, it can be utilized in the development of a therapeutic drug, a prophylactic drug, and the like that is particularly effective for Asian people, such as Japanese people.

Furthermore, in accordance with this constitution also, since a peptide is obtained that binds to an HLA-A2 molecule, which is often seen in European and American people in addition to Japanese people, it can be utilized in the development of a therapeutic drug, a prophylactic drug, and the like that is particularly effective for European and American people in addition to Japanese people.

Furthermore, the amino acid sequence contained in the HLA-binding peptide may be an amino acid sequence derived from a certain genome protein of an avian influenza virus, but is not particularly limited. For example, it may be an amino acid sequence derived from an HIV protein, an amino acid sequence derived from a cedar pollen protein, and the like. It may also contain an amino acid sequence derived from another pathogenic or allergenic protein.

For example, when an amino acid sequence is contained that is derived from a nucleoprotein of an avian influenza virus, which is described later, an HLA-binding peptide that can be utilized in the prevention, treatment, and the like of a disease caused by the avian influenza virus can be obtained.

<Embodiment 2>

In accordance with this embodiment, there is provided an HLA-binding peptide that binds to an HLA-A type molecule, contains an amino acid sequence formed by deletion, substitution, or addition of one or two amino acid residues of the amino acid sequence contained in the above-mentioned HLA-binding peptide, and consists of not less than 8 and not more than 11 amino acid residues.

As described later, even though the constitution includes an amino acid sequence formed by deletion, substitution, or addition of one or a few amino acid residues of a specific amino acid sequence that binds to an HLA-A type molecule, similar effects to those of the HLA-binding peptide related to the above-mentioned embodiment 1 are exhibited.

The amino acid sequences of the nucleoproteins of M22344 strain, AF508607 strain, and AY676037 strain of the avian influenza virus are different from each other in part, but since the correlation between prediction data and experimental data for the −log Kd value is high, that is, a sequence that is determined from prediction data to have binding properties shows a good −log Kd value in experimental data, it can be predicted that even an amino acid sequence that is formed by deletion, substitution, or addition of one or two amino acid residues of an amino acid sequence that shows binding properties will show excellent HLA-binding properties in a similar manner.

Furthermore, it can be predicted that even an amino acid sequence formed by deletion, substitution, or addition of one or two amino acid residues of an amino acid sequence shown in SEQ ID NOS: 1 to 52 that has excellent properties in binding to an HLA-A molecule will show excellent HLA-binding properties in a similar manner.

From another viewpoint, it can be predicted that even an amino acid sequence formed by deletion, substitution, or addition of one or a few amino acid residues of an amino acid sequence predicted by the above-mentioned method to have excellent properties in binding to an HLA-A molecule will show excellent HLA-binding properties in a similar manner.

The amino acid residues that are substituted are preferably amino acid residues having similar properties to each other, such as both being hydrophobic amino acid residues.

Moreover, the HLA-binding peptides described in Embodiment 1 and Embodiment 2 can be produced using a method known to a person skilled in the art. For example, they may be artificially synthesized by a solid-phase method or a liquid-phase method. Alternatively, these HLA-binding peptides may be produced by expressing them from a DNA fragment or a recombinant vector coding for these HLA-binding peptides. These HLA-binding peptides thus obtained can be identified by a method known to a person skilled in the art. For example, identification is possible by use of Edman degradation, mass spectrometry, and the like.

<Embodiment 3>

In accordance with the present embodiment, there is provided a DNA fragment containing a DNA sequence coding for the above-mentioned HLA-binding peptide. Since the DNA fragment related to the present embodiment contains a specific DNA sequence, it can express the above-mentioned HLA-binding peptide.

When the above-mentioned HLA-binding peptide is expressed by using the DNA fragment related to the present embodiment, expression may be carried out by incorporating this DNA fragment into a cell, or expression may be carried out by using a commercial artificial protein expression kit.

Furthermore, continuous expression may be carried out by incorporating the above-mentioned DNA fragment into, for example, a human cell. Because of this, an HLA-binding peptide can be made to be present continuously within a cell by incorporating a DNA fragment coding for the HLA-binding peptide into the cell rather than incorporating the HLA-binding peptide itself into the cell. When an HLA-binding peptide is used as a vaccine, such an ability to express continuously is advantageous in terms of enhancing the efficacy of the vaccine.

Moreover, the DNA fragment related to the present embodiment can be produced by a method known to a person skilled in the art. For example, it may be artificially synthesized by means of a commercial DNA synthesizer and the like. Alternatively, it may be segmented from the HCV genome by using a restriction enzyme and the like. Alternatively, it may be amplified from the HCV genome by a PCR method using a primer. The DNA fragment thus obtained may be identified using a method known to a person skilled in the art. For example, it may be identified by a commercial DNA sequencer.

<Embodiment 4>

In accordance with the present embodiment, there is provided a recombinant vector that contains a DNA sequence coding for the above-mentioned HLA-binding peptide. Since the recombinant vector related to the present embodiment contains a specific DNA sequence, the above-mentioned HLA-binding peptide can be expressed.

When the above-mentioned HLA-binding peptide is expressed by using the recombinant vector related to the present embodiment, expression may be carried out by incorporating this recombinant vector into a cell, or expression may be carried out by using a commercial artificial protein expression kit.

Furthermore, continuous expression may be carried out by incorporating the above-mentioned recombinant vector into, for example, a human cell. Because of this, the HLA-binding peptide can be made to be present continuously within a cell by incorporating a recombinant vector coding for the HLA-binding peptide into the cell rather than incorporating the HLA-binding peptide itself into the cell. When the HLA-binding peptide is used as a vaccine, such an ability to express continuously is advantageous in terms of enhancing the efficacy of the vaccine.

Furthermore, in the above-mentioned recombinant vector, the amount of HLA-binding peptide expressed can be controlled with high precision by the use of a certain sequence in a regulatory region involved in transcription and expression, such as a promoter region upstream of a DNA sequence coding for the above-mentioned HLA-binding peptide. Moreover, the copy number of the recombinant vector in a cell can be controlled with high precision by the use of a certain sequence in a regulatory region involved in replication, such as the origin region of the recombinant vector.

Furthermore, the above-mentioned recombinant vector may freely contain a sequence other than the DNA sequence coding for the above-mentioned HLA-binding peptide. For example, it may contain a sequence of a marker gene such as a drug resistance gene.

Moreover, the recombinant vector related to the present embodiment can be produced using a method known to a person skilled in the art. For example, it may be obtained by cleaving a multicloning site of a commercial vector such as pBR322 or pUC19 at a certain restriction enzyme site, and inserting the above-mentioned DNA fragment into the site and carrying out ligation. Furthermore, the recombinant vector thus obtained can be identified using a method known to a person skilled in the art. For example, it can be confirmed by agarose gel electrophoresis whether or not the length of the DNA fragment cleaved by a predetermined restriction enzyme coincides with the restriction map of a commercial vector such as pBR322 or pUC19 and, furthermore, it can be identified by a DNA sequencer and the like whether or not the above-mentioned DNA sequence is contained in the DNA sequence cut out from the multicloning site.

Embodiments of the present invention are described above, but they are exemplifications of the present invention, and various constitutions other than those above may be employed.

For example, in the embodiments above, an HLA-binding peptide containing an amino acid sequence derived from a certain genome protein of avian influenza virus is used, but an HLA-binding peptide containing an amino acid sequence derived from another protein of avian influenza virus may be used. In such a case, it can be utilized in the treatment of various immune diseases related to the protein from which it is derived.

Furthermore, it may be an HLA-binding peptide for a pathogen other than avian influenza virus, such as an HIV virus, or an allergen such as cedar pollen, or an HLA-binding peptide containing an amino acid sequence derived from a protein such as a cancer cell.

It can be anticipated that if an amino sequence is contained that is predicted using the above-mentioned method to have excellent binding to HLA, it will shown excellent binding properties to HLA in a similar manner when it is experimentally confirmed. Because of this, these HLA-binding peptides can be used suitably in treatment or prevention centering around infectious diseases (influenza, SARS, HIV, HCV, and the like), and in cancer immunotherapy, allergic disease (hay fever, rheumatism, atopy, asthma, and the like), autoimmune disease, and the like.

EXAMPLES

The present invention is further explained below by reference to Examples, but the present invention is not limited thereto.

Specifically, procedures of prediction, experiment, and evaluation in the present examples were carried out based on an active learning experiment design, and in general the following steps were repeated. A schematic drawing for the active learning experiment design employed here is shown in FIG. 1.

(1) A trial of a lower-order learning algorithm, which will be described later, was carried out once. That is, a plurality of hypotheses were generated by random sampling from accumulated data and, with regard to randomly expressed candidate query points (peptides), a point that showed the largest distribution of predicted values was selected as a query point to be subjected to an experiment.

(2) The peptide at the selected query point was prepared by a synthesis and purification method, which will be described later, and the actual binding ability was measured by an experiment, which will be described later, and added to accumulated data.

In the present example, as the lower-order learning algorithm, a supervised learning algorithm of a Hidden Markov Model was used, and 20 to 30 types of peptides were predicted and selected per experiment by starting with the initial data for 223 types of peptides; the above-mentioned procedure was repeated four times, and a total of 341 data points were obtained.

More specifically, in the active learning method of the present example, 20 to 30 types of peptides containing an amino acid sequence in which 9 of 20 types of amino acids were arranged were designed and synthesized per experiment. The strength of binding (binding ability) thereof to an HLA molecule was measured. The binding ability (Kd value) was obtained as an experimental result. When the binding ability was high, the peptide was selected as a candidate for an HLA-binding peptide that could be used as a material for a vaccine.

The results thus obtained were inputted into a learning system equipped with a learning machine employing the Hidden Markov Model as a mathematical algorithm, and rules were created. The learning machine sampled different results to prepare the rules. The rules expressed by the learning machine had different constitutions. The rules thus obtained and experimental data were stored as needed as accumulated data.

From among more than $20^9$=500 billion peptide sequences, candidates for a subsequent experiment were selected by the rules, and the above-mentioned process was repeated. In this stage, different rules were applied to experimental candidates, and the candidates for which predictions of the experimental results were divided were subjected to experiment. In this way, since the candidates for which predictions of the experimental results were divided were subjected to subsequent experiment, the final precision of the prediction was increased.

In this way, a plurality of learning machines carried out selective sampling in which samples that would give different predictions were selected as experimental candidates, information could be gained efficiently, and a hypothesis (rule) with high precision could be obtained. Repeating the above-mentioned process four times gave excellent results as in Examples described later. Repeating it seven times or more gave even better results.

In accordance with such an active learning method, the number of repetitions of the binding experiment for peptides consisting of 9 amino acid residues, which would otherwise have to be carried out for the 500 billion or more combinations of all the candidates for HLA-binding peptides, could be reduced. In the active learning method, a rule was formed by experiment, and the experiment was repeated for tens of sequence candidates that were predicted by applying the rule. Because of this, the number of experiments could be cut, and the time and cost of the initial screening could be greatly reduced.

Furthermore, the hit rate for prediction of the binding of a peptide to HLA by the rule obtained by the active learning method reached 70 to 80%, whereas the hit rate by other known techniques such as the anchor method was as low as about 30%.

<Synthesis and Purification of Peptide>

A peptide was manually synthesized by the Merrifield solid-phase method using Fmoc amino acids. After deprotection, reverse phase HPLC purification was carried out using a C18 column to give a purity of 95% or higher. Identification of the peptide and confirmation of its purity were carried out using a MALDI-TOF mass spectrometer (Voyager DE RP, PerSeptive). Quantitative analysis of the peptide was carried out by a Micro BCA assay (Pierce Corp.) using BSA as a standard protein.

<Experiment of Binding Peptide to HLA-A2402 Molecule>

The ability of a peptide to bind to an HLA-A24 molecule, which is a product of the HLA-A*2402 gene, was measured using C1R-A24 cells expressing the HLA-A24 gene (cells produced by Professor Masafumi Takiguchi, Kumamoto University being supplied with permission).

C1R-A24 cells were first exposed to acidic conditions at a pH of 3.3 for 30 seconds, thus dissociating and removing a light chain β2m, which is associated with HLA class I molecules in common, and an endogenous peptide originally bound to the HLA-A*2402 molecule. After neutralization, purified β2m was added to C1R-A24 cells, the obtained product was added to serial dilutions of a peptide, and incubated on ice for 4 hours. Staining was carried out using fluorescently labeled monoclonal antibody 17A12, which recognizes association (MHC-pep) of the three members, that is, HLA-A*2402 molecule, the peptide, and β2m, which had reassociated during the incubation.

Subsequently, the MHC-pep count per C1R-A24 cell (proportional to the strength of fluorescence of the above-mentioned fluorescent antibody) was quantitatively measured using a FACScan fluorescence-activated cell sorter (Becton Dickinson Biosciences). A binding dissociation constant Kd value between the HLA-A24 molecule and the peptide was calculated from the average strength of fluorescence per cell by a published method (Udaka et al., Immunogenetics, 51, 816-828, 2000).

<Experiment of Binding Peptide to HLA-A0201 Molecule>

The ability of a peptide to bind to an HLA-A2 molecule, which is a product of the HLA-A*0201 gene, was measured using strain JY cells (obtained from ATCC (American Type Culture Collection)) expressing the HLA-A*0201.

JY cells were first exposed to acidic conditions at a pH of 3.8 for 30 seconds, thus dissociating and removing a light chain β2m and an endogenous peptide, which were noncovalently associated with the HLA-A*0201 molecule. After neutralization, a reassociation experiment was carried out.

The above-mentioned JY cells and the purified β2m were added to stepped dilutions of peptide for which the binding ability would be measured, and incubation was carried out on ice for 4 hours. HLA-A*0201 molecules that had reassociated up to this point were stained using the associating type specific fluorescently-labeled monoclonal antibody BB7.2.

Subsequently, the amount of fluorescence per cell was measured using a flow cytometer and a dissociation constant Kd value was calculated by a published method (Udaka et al., Immunogenetics, 51, 816-828, 2000).

<Experiment of Binding Peptide to HLA-A0206 Molecule>

The ability of a peptide to bind to an HLA-A2 molecule, which is a product of the HLA-A*0206 gene, was measured using RA2.6 cells (cell strain newly prepared in Kochi University) in which cDNA of the HLA-A*0206 gene is expressed in RAMS cells, which are mouse TAP peptide transporter deficient cells.

RA2.6 cells were first cultured overnight at 26° C.; when HLA-A*0206 molecules having no peptide bound thereto were deposited on the cell surface, stepped dilutions of peptide were added; binding was carried out at room temperature for 30 minutes.

Subsequently, culturing was carried out at 37° C. for 3.5 hours, empty HLA-A*0206 molecules to which no peptide was bound were denatured, and the tertiary structure was lost.

The cells were stained by adding thereto fluorescently labeled monoclonal antibody 17A10 or 17A12, which specifically recognize the peptide-binding HLA-A*0206 molecule, and incubating on ice for 20 minutes.

Subsequently, the amount of fluorescence per cell was measured using a flow cytometer, and a dissociation constant Kd value was calculated by a published method (Udaka et al., Immunogenetics, 51, 816-828, 2000).

<Evaluation Results>

The prediction results and the experimental results shown in Table 1 to Table 3 above were obtained.

The sequences of SEQ ID NOS: 1 to 20 in Table 1 are sequences consisting of 9 amino acid residues contained in the full-length sequence of a nucleoprotein of M22344 strain, AF508607 strain, or AY676037 strain of avian influenza virus registered in GENBANK. The sequences of SEQ ID NOS: 1 to 20 are sequences predicted by a hypothesis obtained using the experimental design method explained in Embodiment 1 to be the highest in terms of binding to an HLA-A24 molecule (a product of the HLA-A*2402 gene). SEQ ID NOS: 1 to 20 are arranged in decreasing binding order. That is, SEQ ID NO: 1 is the sequence that is predicted to have the best binding. The full-length amino acid sequence of the nucleoprotein of M22344 strain of avian influenza virus is shown in SEQ ID NO: 53 (MASQGTKRSYEQMETGGERQNATEIRASVGRMVGGIGRFYIQMCTELKLSDYEGRLI QNSITIERMVLSAFDERRNKYLEEHPSAGKDPKKTGGPIYKRRDGKWMRELILYDKEE IRRIWRQANNGEDATAGLTHLMIWHSNLNDATYQRTRALVRTGMDPRMCSLMQGSTLP RRSGAAGAAVKGVGTMVMELIRMIKRGINDRNFWRGENGRRTRIAYERMCNILKGKFQ TAAQRAMMDQVRESRNPGNAEIEDLIFLARSALILRGSVAHKSCLPACVYGLAVASGY DFEREGYSLVGIDPFRLLQNSQVFSLIRPNENPAHKSQLVWMACHSAAFEDLRVSSFI RGTRVVPRGQLSTRGVQIASNENMETMDSSTLELRSRYWAIRTRSGGNTNQQRASAGQ ISVQPTFSVQRNLPFERATIMAAFTGNTEGRTSDMRTEIIRMMESARPEDVSFQGRGV FELSDEKATNPVVPSFDMSNEGSYFFGDNAEEYDN), the full-length amino acid sequence of the nucleoprotein of AF508607 strain is shown in SEQ ID NO: 54 (MALQGTKRSYEQMETGGERQNATEIRASVGRMVGGIGRFYIQMCTELKLSDHEGRLI QNSITIERMVLSAFDERRNRYLEENPSAGKDPKKTGGPIYKRREGKWVRELILYDKEE IRRIWRQANNGEDATAGLTHLMIWHSNLNDATYQRTRALVRTGMDPRMCSLMQGSTLP RRSGAAGAAVKGIGTMVMELIRMIKRGINDRNFWRGDNGRRTRIAYERMCNILKGKFQ TEAQRAMMDQVRESRNPGNAEIEDLIFLARSALILRGSVAHKSCLPACVYGLAVASGY DFEREGYSLVGIDPFRLLQNSQVFSLIRSNENPAHKSQLVWMACHSAAFEDL- RVSSFI RGTRVIPRGQLSTRGVQIASNEN-METIDSSTLELRSRYWAIRTRSGGNTNQHRASAGQ ISVQPTFSVQRSLPFERATIMAAFTGN-TEGRTSDMRTEIIRMMENAKPEDVSFQGRGV FELSDEKATSPIVPSFDMSNEGSYFFGDNAEEYD), and the full-length amino acid sequence of the nucleoprotein of AY676037 strain of avian influenza virus is shown in SEQ ID NO: 55 (MASQGTKRSYEQMETGGERQNATEIRAS-VGRMVSGIGRFYIQMCTELKLSDYEGRLI QNSITIER-MVLSAFDERRNRYLEEHPSAGKDPKKTG-GPIYRRRDGKWVRELILYDKEE IRRIWRQANNGEDATAGLTHLMIWH-SNLNDATYQRTRALVRTGMDPRMCSLMQGSTLP RRSGAAGAAVKGVGTMVME-LIRMIKRGINDRNFWRGENGRRTRIAY-ERMCNILKGKFQ TAAQRAMMDQVRESRNPG-NAEIEDLIFLARSALILRGSVAHKSCLPACVYGLAVASGY DFEREGYSLVGIDPFRLLQNSQVFSLIR-PNENPAHKSQLVWMACHSAAFEDLRVSSFI RGTRV-VPRGQLSTRGVQIASNENMEAMD-SNTLELRSRYWAIRTRSGGNTNQQRASAGQ ISVQPTFSVQRNLPFERATIMAAFTGN-TEGRTSDMRTEIIRMMESARPEDVSFQGRGV FELSDEKATNPIVPSFDMNNEGSYFFGDNAEEYDN).

Furthermore, the sequences of SEQ ID NOS: 21 to 36 in Table 2 are sequences consisting of 9 amino acid residues contained in a nucleoprotein of M22344 strain, AF508607 strain, or AY676037 strain of the above-mentioned avian influenza virus. The sequences of SEQ ID NOS: 21 to 36 are sequences predicted by a hypothesis obtained using the experimental design method explained in Embodiment 1 to be the highest in terms of binding to an HLA-A2 molecule (a product of the HLA-A*0201 gene). SEQ ID NOS: 21 to 36 are arranged in decreasing binding order. That is, SEQ ID NO: 21 is the sequence that is predicted to have the best binding.

Moreover, the sequences of SEQ ID NOS: 37 to 52 in Table 3 are sequences consisting of 9 amino acid residues contained in a nucleoprotein of M22344 strain, AF508607 strain, or AY676037 strain of the above-mentioned avian influenza virus. The sequences of SEQ ID NOS: 37 to 52 are sequences predicted by a hypothesis obtained using the experimental design method explained in Embodiment 1 to be the highest in terms of binding to an HLA-A2 molecule (a product of the HLA-A*0206 gene). SEQ ID NOS: 37 to 52 are arranged in decreasing binding order. That is, SEQ ID NO: 37 is the sequence that is predicted to have the best binding.

Table 1 to Table 3 show, with regard to each of the nucleoproteins of M22344 strain, AF508607 strain, or AY676037 strain of avian influenza virus, the amino acid sequences with the highest scores in the predicted results obtained using the above-mentioned prediction program, the predicted score, and the corresponding binding experiment data. All of the binding experiments were obtained by artificially synthesizing a 9-amino acid peptide by the above-mentioned synthetic method.

Although the amino acid sequences of the nucleoproteins of avian influenza virus M22344 strain, AF508607 strain, and AY676037 strain are registered in GenBank, sequences consisting of 9 amino acid residues thereamong, which become HLA-binding peptides, are not currently registered.

There are a plurality of serum types for the avian influenza virus that have a possibility of infecting humans; among them M22344 strain (H7 type) is the type of influenza that is currently (as of November 2005) spreading mainly in Europe, and AY676037 strain (H5 type) is the type of influenza that is currently spreading mainly in Asian but also in Europe. In this example, an HLA-binding peptide contained in the nucleoprotein of such an influenza virus epidemic strain, which is spreading in Europe or Asia, has been found. This HLA-binding peptide can suitably be utilized in the development of preventive/therapeutic vaccines for avian influenza in Europe and Asia.

Here, the amino acid sequences of the nucleoproteins of M22344 strain, AF508607 strain, and AY676037 strain of the avian influenza virus are different from each other in part, but it can be predicted that even amino acid sequences in which one or a few amino acid residues of the amino acid sequences are substituted for each other will show excellent HLA-binding properties in the same way as described above.

For example, the third from the left in the SEQ ID NO: 7 peptide of the M22344 strain is N, whereas in the SEQ ID NO: 9 peptide of the AF508607 strain it is S instead of N, and the fifth from the left in the SEQ ID NO: 7 peptide of the M22344 strain is V, whereas in the SEQ ID NO: 9 peptide of the AF508607 strain and the SEQ ID NO: 6 peptide of the AY676037 strain it is I instead of V.

Furthermore, for example, the first from the left in the SEQ ID NO: 8 peptide of the M22344 strain is N, whereas in the SEQ ID NO: 11 peptide of the AF508607 strain it is S instead of N.

Moreover, for example, the fourth from the left in the SEQ ID NO: 14 peptide of the M22344 strain is G, whereas in the SEQ ID NO: 15 peptide of the AY676037 strain it is S instead of G.

Furthermore, for example, the third from the left in the SEQ ID NO: 16 peptide of the M22344 strain is S, whereas in the SEQ ID NO: 18 peptide of the AY676037 strain it is N instead of S.

Moreover, for example, the sixth from the left in the SEQ ID NO: 17 peptide of the M22344 strain is D, whereas in the SEQ ID NO: 13 peptide of the AF508607 strain it is E instead of D, and the third from the left in the SEQ ID NO: 17 peptide of the M22344 strain is K, whereas in the SEQ ID NO: 10 peptide of the AY676037 strain it is R instead of K.

Furthermore, for example, the fifth from the left in the SEQ ID NO: 21 peptide of the M22344 strain is H, whereas in the SEQ ID NO: 26 peptide of the AF508607 strain it is N instead of H.

Moreover, for example, the fifth from the left in the SEQ ID NO: 23 peptide of the M22344 strain is V, whereas in the SEQ ID NO: 27 peptide of the AF508607 strain it is I instead of V.

Among the peptide sequences in which single amino acid residues are substituted for each other, for example, the third from the left in the SEQ ID NO: 7 peptide of the M22344 strain is N, whereas in the SEQ ID NO: 9 peptide of the AF508607 strain it is S instead of N, and the experimental binding value for the SEQ ID NO: 7 peptide of the M22344 strain is 7.80781, whereas the experimental binding value for the SEQ ID NO: 9 peptide of the AF508607 strain is 7.80229. Furthermore, the fifth from the left in the SEQ ID NO: 7 peptide of the M22344 strain is V, whereas in the SEQ ID NO: 9 peptide of the AF508607 strain and the SEQ ID NO: 6 peptide of the AY676037 strain it is I instead of V, and the experimental binding value for the SEQ ID NO: 7 peptide of the M22344 strain is 7.80781, whereas the experimental binding value for the SEQ ID NO: 9 peptide of the AF508607 strain is 7.80229 and the experimental binding value for the SEQ ID NO: 6 peptide of the AY676037 strain is 7.56449, thus confirming that binding is good in all cases.

Furthermore, among the peptide sequences in which single amino acid residues are substituted for each other, for example, the first from the left in the SEQ ID NO: 8 peptide of the M22344 strain is N, whereas in the SEQ ID NO: 11 peptide of the AF508607 strain it is S instead of N, and the experimental binding value for the SEQ ID NO: 8 peptide of the M22344 strain is 7.76375, whereas the experimental binding value for the SEQ ID NO: 11 peptide of the AF508607 strain is 7.71879, thus confirming that binding is good in either case.

Moreover, among the peptide sequences in which single amino acid residues are substituted for each other, for example, the fourth from the left in the SEQ ID NO: 14 peptide of the M22344 strain is G, whereas in the SEQ ID NO: 15 peptide of the AY676037 strain it is S instead of G, and the experimental binding value for the SEQ ID NO: 14 peptide of the M22344 strain is 7.54336, whereas the experimental binding value for the SEQ ID NO: 15 peptide of the AY676037 strain is 7.43594, thus confirming that binding is good in either case.

Furthermore, among the peptide sequences in which single amino acid residues are substituted for each other, for example, the third from the left in the SEQ ID NO: 16 peptide of the M22344 strain is S, whereas in the SEQ ID NO: 18 peptide of the AY676037 strain it is N instead of S, and the experimental binding value for the SEQ ID NO: 16 peptide of the M22344 strain is 5.74415, whereas the experimental binding value for the SEQ ID NO: 18 peptide of the AY676037 strain is 5.37438, thus confirming that binding is good in either case.

Moreover, among the peptide sequences in which single amino acid residues are substituted for each other, for example, the sixth from the left in the SEQ ID NO: 17 peptide of the M22344 strain is D, whereas in the SEQ ID NO: 13 peptide of the AF508607 strain it is E instead of D, and the experimental binding value for the SEQ ID NO: 17 peptide of the M22344 strain is 7.32598 whereas the experimental binding value for the SEQ ID NO: 13 peptide of the AF508607 strain is 7.25015. Furthermore, the third from the left in the SEQ ID NO: 17 peptide of the M22344 strain is K, whereas in the SEQ ID NO: 10 peptide of the AY676037 strain it is R instead of K, and the experimental binding value for the SEQ ID NO: 17 peptide of the M22344 strain is 7.32598, whereas the experimental binding value for the SEQ ID NO: 10 peptide of the AY676037 strain is 7.49653, thus confirming that binding is good in all cases.

Furthermore, among the peptide sequences in which single amino acid residues are substituted for each other, for example, the fifth from the left in the SEQ ID NO: 21 peptide of the M22344 strain is H, whereas in the SEQ ID NO: 26 peptide of the AF508607 strain it is N instead of H, and the experimental binding value for the SEQ ID NO: 21 peptide of the M22344 strain is 5.08483, whereas the experimental binding value for the SEQ ID NO: 26 peptide of the AF508607 strain is 4.90353, thus confirming that binding is good in either case.

Moreover, among the peptide sequences in which single amino acid residues are substituted for each other, for example, the fifth from the left in the SEQ ID NO: 23 peptide of the M22344 strain is V, whereas in the SEQ ID NO: 27 peptide of the AF508607 strain it is I instead of V, and the experimental binding value for the SEQ ID NO: 23 peptide of the M22344 strain is 5.57857 whereas the experimental binding value for the SEQ ID NO: 27 peptide of the AF508607 strain is 4.8085, thus confirming that binding is good in either case.

It can therefore be predicted that any of the peptide sequences in which one or two amino acid residues are substituted for each other will show excellent binding to an HLA-A molecule. In conclusion, even an amino acid sequence formed by deletion, substitution, or addition of one or a few amino acid residues of an amino acid sequence shown by SEQ ID NOS: 1 to 52 that has excellent properties in binding to an HLA-A molecule can be predicted to similarly show excellent HLA-binding properties.

From another viewpoint, even an amino acid sequence formed by deletion, substitution, or addition of one or a few amino acid residues of an amino acid sequence that has excellent properties in binding to an HLA-A molecule as predicted by the hypothesis obtained by the experimental design method explained in Embodiment 1 similarly can be said to show excellent HLA-binding properties. The amino acid residues that are substituted are preferably amino acid residues that have similar properties to each other, such as the two being hydrophobic amino acid residues.

The present invention is explained above by reference to Examples. These Examples are only illustrated as examples, and a person skilled in the art will understand that various modification examples are possible, and such modification examples are included in the scope of the present invention.

For example, in the examples above, the nucleoprotein of the M22344 strain, AF508607 strain, or AY676037 strain of avian influenza virus was used, but another protein or another strain of the avian influenza virus may be used. In this case also, in accordance with the prediction program used in the present invention, HLA binding properties can be predicted with high accuracy.

The invention claimed is:

1. An HLA-binding peptide binding to an HLA-A type molecule, said HLA-binding peptide consisting of one sequence selected from the group consisting of SEQ ID NOS: 2, 9, 13, 19, 20, 22, 24, 26-30, 32-34, 37, 40-43, 45, 47-49, 51 and 52
wherein said HLA-binding peptide is included in an amino acid sequence of a nucleoprotein of AF508607 strain which is represented by SEQ ID NO: 54, wherein said HLA-binding peptide binds to a human HLA-A*2402 molecule.

2. An HLA-binding peptide binding to an HLA-A type molecule, said HLA-binding peptide consisting of one sequence selected from the group consisting of SEQ ID NOS: 2, 9, 13, 19, 20, 22, 24, 26-30, 32-34, 37, 40-43, 45, 47-49, 51 and 52
wherein said HLA-binding peptide is included in an amino acid sequence of a nucleoprotein of AF508607 strain which is represented by SEQ ID NO: 54, wherein said HLA-binding peptide binds to a human HLA-A*0201 molecule.

3. An HLA-binding peptide binding to an HLA-A type molecule, said HLA-binding peptide consisting of one sequence selected from the group consisting of SEQ ID NOS: 2, 9, 13, 19, 20, 22, 24, 26-30, 32-34, 37, 40-43, 45, 47-49, 51 and 52
wherein said HLA-binding peptide included in an amino acid sequence of a nucleoprotein of AF508607 strain which is represented by SEQ ID NO: 54, wherein said HLA-binding peptide binds to a human HLA-A*0206 molecule.

* * * * *